(12) United States Patent
Polack et al.

(10) Patent No.: US 9,493,761 B2
(45) Date of Patent: Nov. 15, 2016

(54) PROCOAGULANT MOLECULAR DECOY FOR TREATING HEMOPHILIA A OR B WITH OR WITHOUT INHIBITOR

(75) Inventors: Benoit Polack, Saint Martin le Vinoux (FR); Aline Thomas, Meylan (FR)

(73) Assignees: UNIVERSITE JOSEPH FOURIER (GRENOBLE 1), Grenoble (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/002,253

(22) PCT Filed: Feb. 29, 2012

(86) PCT No.: PCT/FR2012/050425
§ 371 (c)(1),
(2), (4) Date: Oct. 15, 2013

(87) PCT Pub. No.: WO2012/117203
PCT Pub. Date: Sep. 7, 2012

(65) Prior Publication Data
US 2014/0050716 A1 Feb. 20, 2014

(30) Foreign Application Priority Data
Mar. 1, 2011 (FR) ...................... 11 51637

(51) Int. Cl.
*C12N 9/64* (2006.01)
*A61K 38/48* (2006.01)

(52) U.S. Cl.
CPC ......... *C12N 9/6432* (2013.01); *A61K 38/4846* (2013.01); *C12Y 304/21006* (2013.01)

(58) Field of Classification Search
None
See application file for complete search history.

(56) References Cited

U.S. PATENT DOCUMENTS

2009/0098119 A1* 4/2009 Lu ...................... A61K 38/4826
424/133.1

FOREIGN PATENT DOCUMENTS

| WO | WO2009/042962 | * | 4/2009 | ............... C12N 9/64 |
| WO | WO 2009/042962 A2 | | 4/2009 | |

OTHER PUBLICATIONS

Skogen et al., "Comparison of coagulation factor Xa and des-(1044) factor Xa in the assembly of prothrombinase," Jl. of Biol. Chem., vol. 259, No. 4, Feb. 1984, pp. 2306-2310.*
Tjonnfjord and Holme, Factor eight bypass activity (FEIBA) in the management of bleeds in hemophilia patients with high-titer inhibitors, Vasc Mgmt and Risk Mgmt, 2007:3(4)527-531.*
Marlu & Polack, Domain GLA Less Factor Xa: A Molecular Bait to Bypass Tenase Complex, 1ere Journee Scientifique du Medicament: Nouvells Strategies Therapeutiqes, Grenoble, Jun. 23, 2011, p. 25, supplied with IDS.*
Remington: The Science and Practice of Pharmacy, 20th Edition, A. R. Gennaro, Ed., Lippincott Williams & Wilkins, (2000), pp. 721-727.*
NCBI GenBank: AAA51984.1, 1994 (two pages).*
Damodaran V. B. and Fee C. J. (2010). "Protein PEGylation: An overview of chemistry and process considerations". European Pharmaceutical Review 15 (1): 18-26.*
Thiec et al., Role of the Gla and First Epidermal Growth Factor-like Domains of Factor X in the Prothrombinase and Tissue Factor-Factor Vlla Complexes, JBC, vol. 278, No. 12, Issue of Mar. 21, pp. 10393-10399, 2003.*
Marlu & Polack, Domain GLA Less Factor Xa: A Molecular Bait to Bypass Tenase Complex, Iere Journee Scientifique du Medicament: Nouvells Strategies Therapeutiqes, Grenoble, Jun. 23, 2011, p. 25.*
Skogen et al., "Comparison of Coagulation Factor Xa and Des-(1-44)factor Xa in the Assembly of Prothrombinase," The Journal of Biological Chemistry, Feb. 25, 1984, pp. 2306-2310, vol. 259, No. 4, The American Society of Biological Chemists, Inc., US.
Tellier et al., "Management of Haemophilia A-Inhibitor Patients: Clinical and Regulatory Perspectives," Clinical Reviews in Allergy & Immunology, 2009, pp. 125-134, vol. 37, Humana Press Inc.
Venkateswarlu et al., "Structure and Dynamics of Zymogen Human Blood Coagulation Factor X," Biophysical Journal, Mar. 2002, pp. 1190-1206, vol. 82, Biophysical Society.
Marlu et al., "I$^{ADDAC:Agere}$ Journée Scientifique du Médicament: Nouvelles Stratégies Thérapeutiques," Jun. 23, 2011, pp. 1-43, Grenoble, FR.
International Search Report issued in International Application No. PCT/FR2012/050425 dated May 18, 2012.

* cited by examiner

*Primary Examiner* — Lianko Garyu
*Assistant Examiner* — Joseph Fischer
(74) *Attorney, Agent, or Firm* — Joel S. Armstrong

(57) ABSTRACT

The present invention relates to a pharmaceutical composition including a modified factor Xa (GDXa), said modified GDXa being nonthrombogenic, able to bind to TFPI but not able to bind to phospholipids, for preventing or treating a hemorrhagic accident in a patient with hemophilia A or B with or without inhibitor.

4 Claims, 5 Drawing Sheets

Figure 1:
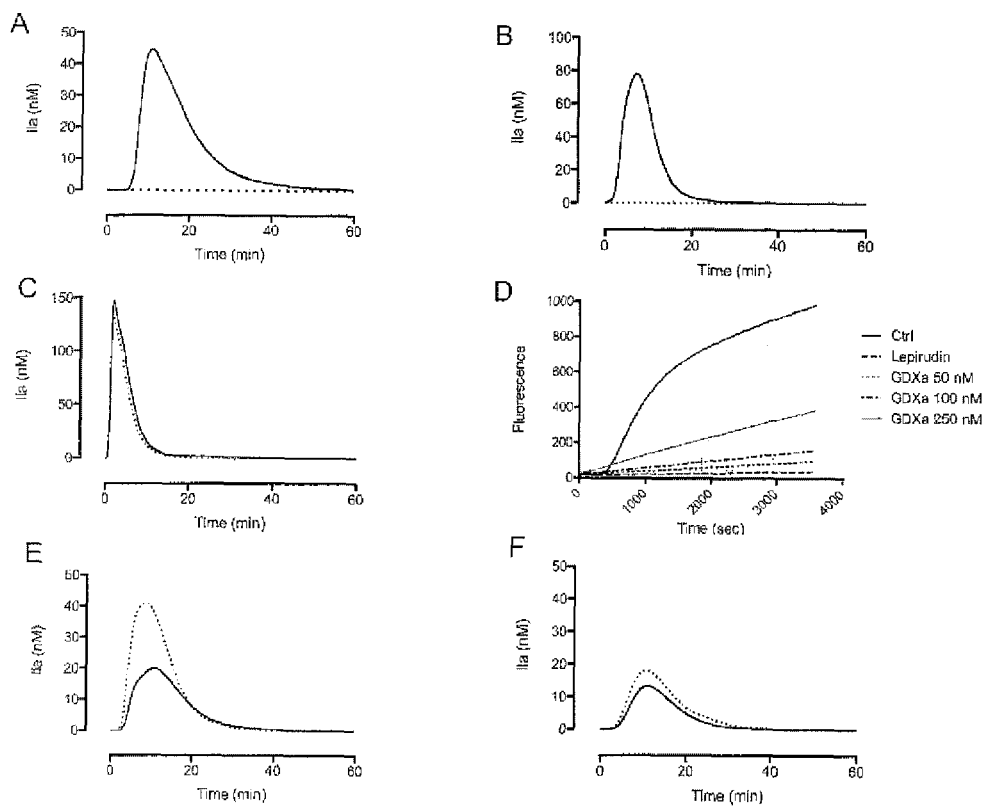

PROCOAGULANT MOLECULAR DECOY FOR TREATING HEMOPHILIA A OR B WITH OR WITHOUT INHIBITOR

The present invention relates to a pharmaceutical composition for preventing or treating a hemorrhagic accident in a patient with hemophilia A or B by means of a modified factor X.

Hemophilia A, like hemophilia B, includes two types of hemophilia, constitutional hemophilia and acquired hemophilia.

Type A constitutional hemophilia is a hemorrhagic disease characterized by a quantitative or qualitative deficiency of FVIII resulting from an abnormality of the FVIII gene. Type B constitutional hemophilia is also a hemorrhagic disease but is characterized by a quantitative or qualitative deficiency of FIX resulting from an abnormality of the FIX gene.

Acquired hemophilia of type A or B is defined by the appearance of autoantibodies directed against said FVIII or FIX.

Hemophilia is reflected in a deficiency of blood coagulation in response to a hemorrhage. Untreated type A or B hemophiliacs have symptoms such as excessive bleeding if injured and sometimes even spontaneous hemorrhages.

The biological activity of factors VIII or IX is evaluated as a percentage of the normal level. A normal individual is considered to have 100% activity. If the activity is undetectable (below 1%), it is severe hemophilia, if the activity is between 1 and 5% the hemophilia is said to be moderate; above that and up to 30% it is minor hemophilia.

Patients with hemophilia A and B can be treated with concentrates comprising FVIII or FIX respectively, which can be plasma derivatives or products resulting from genetic engineering. These concentrates can be administered on the occasion of each hemorrhage, and in this case it is advisable to commence treatment as quickly as possible, on appearance of the first signs. The treatment can also be administered prophylactically, regularly 2 to 3 times per week so as to prevent hemorrhages. However, the treatment can give rise to the appearance of antibodies directed against FVIII or FIX called inhibitors. The presence of said antibodies then makes the administrations of factors VIII or IX ineffective. These antibodies are class G immunoglobulins, predominantly IgG4. They develop soon after the first administrations, often before the tenth. Some patients remain poor responders (antibody titer<10 BU), others called strong responders reach titers that mean they can no longer be treated with the corresponding factor.

At the date of the present invention, no treatment exists that can satisfactorily prevent and/or treat the existence of a hemorrhagic risk in patients with hemophilia A or B who have an inhibitor. In fact, the available products may be ineffective (Astermark J, Donfield S M, DiMichele D M, Gringeri A, Gilbert S A, Waters J, Berntorp E, for the FSG. A randomized comparison of bypassing agents in hemophilia complicated by an inhibitor: the FEIBA NovoSeven Comparative (FENOC) Study. Blood. 2007; 109: 546-51) or their administration may be complicated by thrombotic events (Aledort L M. Comparative thrombotic event incidence after infusion of recombinant factor VIIa versus factor VIII inhibitor bypass activity. J Thromb Haemost. 2004; 2: 1709.).

There is therefore a known need for therapeutic alternatives to the existing treatments. However, development of such a treatment has proved very difficult, as it must:

be able to stop the hemorrhage,
not cause thrombosis,
permit treatment or prevention of hemorrhagic accidents even in the presence of anti-FVIII or FIX antibodies.

The present invention answers this need; it relates to a pharmaceutical composition comprising a modified activated factor X (FXa), said modified FXa (GDXa) being nonthrombogenic and able to bind to the tissue factor pathway inhibitor (TFPI) but not possessing a phospholipid binding site—for preventing or treating a hemorrhagic accident in a patient with hemophilia A or B.

The composition according to the invention can also be used for preventing or treating a hemorrhagic accident in hemophiliacs presenting anti-factor VIII (FVIII) or factor IX (FIX) antibodies. The antibodies appeared either following treatment with factors FVIII or FIX or spontaneously such as in acquired hemophilia.

The present invention also relates to the use of a pharmaceutical composition comprising a modified factor Xa (GDXa) for preparing a medicinal product intended for preventing or treating a hemorrhagic accident in a patient with hemophilia A or B, said patient having or not having anti-FVIII or FIX antibodies.

The present invention also relates to a method of preventive treatment of a hemorrhagic syndrome in a patient with hemophilia A or B by administering a modified factor Xa (GDXa).

The present invention also relates to a method of treatment of a hemorrhagic accident in a patient with hemophilia A or B by administering a modified factor Xa (GDXa).

In the context of the present invention, mention of factor FXa refers to the activated factor X obtained by activation of the native factor X naturally present in the plasma or in the isolated state in its original, unmodified form. This term includes the FXs isolated from the plasma but also the FXs produced recombinantly or obtained by chemical synthesis that have been activated. Factor Xa or native factor Xa (FXa) refers, in the context of the present invention, to a protein of the serine protease type involved in coagulation and which is produced in an inactive form, factor X (FX).

Activation of the clotting factor X is a key step in blood coagulation and stopping of hemorrhages. Its activation is necessary for the steps of propagation and amplification of coagulation. Its activation is also necessary for stopping the activation of coagulation through its interaction with TFPI.

FX is activated either by activated factor IX and its cofactor, activated factor VIII, or by the activated factor VII and its cofactor, the tissue factor (TF). FXa forms the complex prothrombinase, which is bound to the membranes with the activated factor V and is the active component in the complex prothrombinase, which catalyzes the conversion of prothrombin to thrombin. In its turn, thrombin catalyzes the conversion of fibrinogen to fibrin, which leads to the formation of clots in the blood and stoppage of bleeding. The activity of FXa can be called "procoagulant activity".

Leytus et al. (Biochemistry, 1986, 25: 5098-5102) and Venkateswarlu et al. (Biophysical Journal, 2002, 82: 1190-1206) describe factor X and the various domains present in this polypeptide. Catalytic cleavage of the heavy chain permits activation of FX to FXa. FXa comprises a light chain, an example of which is represented by the sequence identifier SEQ ID No. 1 and a heavy chain, an example of which is represented by the sequence identifier SEQ ID No. 2.

In the context of the present invention, the term modified FXa denotes FXa that can no longer bind to phospholipids, no longer possessing procoagulant activity or a reduced procoagulant activity. In the context of the present invention, such a factor is called GDXa. "Procoagulant activity" is defined as the capacity of a factor to cause blood coagulation or the formation of clots. A reduced procoagulant activity signifies that the activity is reduced by at least 50%, preferably at least 90% and even more preferably by more than 95% relative to the activity of the native FXa.

The modified factor Xa according to the invention, GDXa, lacks its γ-carboxyglumatic acid (Gla) domain for binding to phospholipids. The first 43 amino acids of the light chain (residues 1-43 of SEQ ID No. 1) represent the Gla domain as it contains 11 post-translationally modified residues (γ-carboxyglutamic acid). Digestion with chymotrypsin makes it possible to suppress the residues 1-43, making it possible to generate an FXa lacking its domain for binding to phospholipids or GDXa (for Gla Domainless FXa). Said GDXa can also comprise other modifications in addition to absence of its Gla domain. Said modified FXa conserves properties of binding to factor Va but does not possess procoagulant activity. An example of GDXa is represented by the sequence identifier SEQ ID No. 7 or by SEQ ID No. 3 for its light chain and by SEQ ID No. 2 for its heavy chain. This absence of procoagulant activity can be defined by its inability to activate coagulation when it is added to plasma in the absence of tissue factor, which differentiates it from native factor Xa.

GDXa can be obtained by cleavage of factor X by proteolysis controlled by chymotrypsin and activation by a specific protease according to one of the usual methods such as that described by Skogen et al. (1984). An example of GDX prior to its activation can be represented by the sequence identifier SEQ ID No. 20 for its nucleotide sequence and SEQ ID No. 28 for its amino acid sequence.

GDXa can be produced by chemical synthesis, either in the form of a single sequence, or in the form of several sequences which are then joined together. This synthesis can be carried out in the solid phase or in solution. These techniques are more particularly described by Atherton and Shepard in "Solid phase peptide synthesis" (IRL Press Oxford, 1989) and by Houbenweyl (in "Methoden der organischen Chemie" [Methods in Organic Chemistry] published by E. Wunsch Vol. 15-1 and 11, Stuttgart, 1974), as well as in the following articles: P. E. Dawson et al. (Science 1994; 266(5186), pp 776-779); G G Kochendoerfer et al. (1999; 3(6), pp 665-671); P E Dawson et al. (2000, 69, Annu. Rev. Biochem., pp 923-960).

GDXa is nonthrombogenic; its absence of procoagulant activity can be defined by an assay measuring thrombin generation (Hemker et al., Thrombosis and Haemostasis. 1993; 70: 617-624, cf. example 4).

GDXa's capacity for binding to TFPI is defined using any assay well known by a person skilled in the art. Such an assay is described in example 1, employing a chromogenic substrate allowing the percentage inhibition of FXa and GDXa by TFPI to be determined.

In another aspect of the invention GDXa lacks its Gla domain but also the domain EGF1 (Epidermal Growth Factor 1). Such an application of the invention can be represented by a composition comprising a GDXa represented by SEQ ID No. 4 for its light chain and by SEQ ID No. 2 for its heavy chain.

In another aspect of the invention GDXa lacks its Gla domain but also the domain EGF2 (Epidermal Growth Factor 2); an example of such a GDXa is represented by the sequence identifier SEQ ID No. 5 for its light chain and by SEQ ID No. 2 for its heavy chain.

In another aspect of the invention GDXa lacks its domain Gla but also the domains EGF1 and EGF2; an example of such a GDXa is represented by the sequence identifier SEQ ID No. 6 for its light chain and by SEQ ID No. 2 for its heavy chain.

According to another aspect of the invention, GDXa consists solely of the heavy chain of FXa. According to a particular embodiment of the invention, such an FXa is represented by the sequence identifier SEQ ID No. 2.

In yet another different aspect, GDXa consists of molecular variants with mutations. Thus, various mutations were introduced into the gene coding for GDXa enabling thrombin generating activity to be maintained and reducing the enzymatic activity on small peptide substrates of the mutants. These mutations can be introduced using the QuickChange kit (Stratagene) and by following the manufacturer's recommendations and according to the publication Wang & Malcolm (1999)—BioTechniques, 26: 680-682. These mutations can relate to the arginine 142 of the heavy chain of GDXa (numbering according to SEQ ID No. 2) which can be mutated to give any other amino acid, preferably phenylalanine (for example SEQ ID No. 10), glycine (for example SEQ ID No. 11), isoleucine (for example SEQ ID No. 12) or tyrosine (for example SEQ ID No. 13). This mutation can relate to replacement of the peptide sequence of human FXa Arg-Gln-Ser-Thr-Arg-Leu (139-143 of the heavy chain) with the equivalent sequence obtained from bovine FXa: Arg-Leu-Ser-Ser-Thr-Leu (for example SEQ ID No. 26). Similarly lysine 82 of the heavy chain (numbering according to SEQ ID No. 2) can also be replaced by an amino acid such as tyrosine (for example SEQ ID No. 9).

The nucleotide sequence coding for GDXa can be synthesized chemically (Young L and Dong Q., 2004, Nucleic Acids Res., April 15; 32(7), Hoover, D. M. and Lubkowski, J. 2002. Nucleic Acids Res., 30, Villalobos A, et al., 2006. BMC Bioinformatics, June 6; 7: 285). The nucleotide sequence coding for GDXa can also be amplified by PCR using suitable primers.

GDXA can also be produced by genetic engineering techniques that are well known by a person skilled in the art. The nucleotide sequence coding for the human factor X can thus be cloned into an expression vector; part of the nucleotide sequence coding for the signal peptide, the propeptide and domain Gla is deleted, a signal peptide is fused, such as that of TIMP-1 (Crombez et al., 2005). The modified factor X thus produced can be activated either by the complex TF-FVIIa, or by any other enzyme that cleaves the bond between arginine 234 and isoleucine 235 (numbering according to Swiss-Prot: P00742.2). Alternatively, GDXa can be produced directly by insertion of a cleavage sequence recognized by furins or any other intracellular enzyme, directly upstream of isoleucine 235; a sequence coding for these amino acids such as arginine-lysine-arginine permits cleavage by furins (Nakayama et al., 1997). To improve cleavage, a sequence arginine-lysine-arginine-arginine-lysine-arginine can be introduced. The DNA coding for said modified FX is inserted in an expression plasmid and inserted in an ad hoc cell line for production thereof (for example the HEK-393E line), the protein thus produced then being purified by chromatography.

These techniques are described in detail in the reference manuals: Molecular cloning: a laboratory manual, 3rd edition—Sambrook and Russel eds., (2001) and Current Protocols in Molecular Biology—Ausubel et al. eds (2007).

Thus, the GDXa's can also be represented by their nucleotide sequences coding for the GDXa's mentioned above, such sequences being represented by the following sequence identifiers: SEQ ID No. 8, SEQ ID No. 16 to SEQ ID No.

19 for the light chains and by SEQ ID No. 15 or SEQ ID No. 21 to 25 and SEQ ID No. 27 for the heavy chain.

A modified factor of this kind is well known from the prior art (Morita and Jackson, 1986; Skogen et al., 1984, Padmanabhan et al., 1993. J. Mol. Biol., 232: 947-966 or US2009/2298119).

The pharmaceutical composition according to the present invention can be formulated as any dosage form necessary for its administration. In particular, in the case of systemic administration, the composition according to the invention can be formulated in the form of sterile lyophilized powder for injection. The pharmaceutical compositions according to the present invention can also be administered nasally or parenterally. They can therefore comprise, in addition to the active principles, any pharmaceutically acceptable formulation additive, known by a person skilled in the art and that is necessary for preparing the pharmaceutical composition in the desired form and notably any excipient capable of stabilizing the lyophilized protein GDXa after reconstitution with an aqueous solution for subsequent injection thereof.

In the case of a hemorrhagic accident, the pharmaceutical composition according to the present invention can be administered at a concentration 10 to 20 times lower than the recombinant FVIIa (Novoseven®), which is administered according to a posology in the range from 90 to 270 μg/kg per dose administered. Thus, according to another aspect, the present invention also relates to a pharmaceutical composition comprising nonthrombogenic GDXa that can bind to TFPI but cannot bind to the phospholipids, for administration of 4.5 to 27 μg/kg per dose administered, with or without inhibitor, to the patient with hemophilia A or B. Said administration can be by the systemic, nasal or parenteral route.

LEGENDS OF THE FIGURES

FIG. 1. Influence of GDXa or FXa on the generation of thrombin (A) Tests of production of thrombin in the presence of phospholipids and of TF in a pool of normal plasma (solid line) and in a pool of plasmas of severe hemophilia A (dotted line). (B) hemophiliac plasma enriched with GDXa (50 nM) in the presence of phospholipids and TF (solid line) and without TF (dotted line). (C) hemophiliac plasma enriched with FXa (50 nM) in the presence of phospholipids with TF (solid line) and without TF (dotted line). (D) Cleavage of the substrate ZGGR-AMC by GDXa. Normal plasma pre-treated-CTI tested in the presence of phospholipids and of IF with and without (Ctrl-curve A) lepirudin 6 μg/ml in the absence (curve B) or in the presence of various concentrations of GDXa (curves C to E). (E) Generation of thrombin in the presence of phospholipids and of TF in hemophiliac plasma enriched with 10 nM (solid line) or 20 nm (dotted line) of GDXa and (F) with 40 nM (thick line) or 200 nm (dotted line) of rFVIIa.

The data are representative of experiments conducted with at least three different plasmas from different severe type A hemophiliacs.

FIG. 2: Influence of anti-AT and anti-TFPI antibodies on thrombin generation in plasmas from hemophiliacs Different concentrations of anti-human antithrombin (A) or anti-human TFPI (B) antibodies were added to a severe hemophiliac plasma A and were then left for thrombin generation. The antibody concentrations are expressed in g/l for the anti-antithrombin antibodies and in mg/l for the anti-TFPI antibodies. The concentration of GDXa is in nM. HP denotes hemophiliac plasma; NP denotes normal plasma.

(A) Curve A shows hemophiliac plasma, curves B to D show different concentrations of antithrombin antibodies added to the hemophiliac plasma; curve E shows addition of 50 nM of GDXa added to the hemophiliac plasma, and curve F shows the normal plasma. (B) Curve A shows hemophiliac plasma, and curves B to D show different concentrations of anti-TFPI antibodies added to the hemophiliac plasma; curve E shows addition of 50 nM of GDXa added to the hemophiliac plasma, and curve F shows the normal plasma.

FIG. 3: Enzymatic inhibition of GDXa and FXa by TFPI or antithrombin (A-B) for inhibition of antithrombin, 1.25 nM of FXa (A) or GDXa (B) were incubated in the presence of increasing concentrations of antithrombin (AT: 0 (curve A) to 500 nM (curve F)) at 37° C. Aliquots were taken at different time points (0 to 90 min) and added to the chromogenic substrate PNAPEP 1025.

(C-D) The inhibition of the activity of FXa (C) or GDXa (D) by TFPI was analyzed by the incubation of enzyme of 0.25 nM at 25° C. for 3 h in buffer A in the presence of increasing concentrations of TFPI (0 to 30 nM for GDXa and 0 to 10 nM for FXa).

The data are representative of two different experiments.

FIG. 4: Determination of the pharmacokinetic properties of GDXa and FXa in the plasma 50 nM FXa (A) or GDXa (B) was added to normal plasma, and the whole was incubated at 37° C. Aliquots were taken at different time intervals and were immediately diluted 25 times in buffer A for determining the residual activity. The half-lives were 1.4±0.1 min for FXa and 1.8±0.1 min for GDXa.

The data are the mean values of two different experiments.

FIG. 5: correction of thrombin generation by rVIIa and GDXa

Addition of GDXa (curves C and D) or rVIIa at different concentrations (curves E and F) in a hemophiliac plasma (HP, curve B). NP: Normal plasma (curve A).

The present invention will be illustrated by the following examples.

EXAMPLE

Example 1

Materials and Methods

Materials:

The pools of frozen plasma from normal patients and individual plasmas from patients with hemophilia A or hemophilia B, the phospholipids TGT, Prionex, Corn Trypsin Inhibitor (CTI), the chromogenic substrate PNAPEP 1025, human factor Xa, human GDXa, and the sheep anti-human thrombin antibodies were obtained from Cryopep (Montpellier, France). Human recombinant TFPI was obtained from Sino Biolocal Inc. (Beijing, China). The relipidized recombinant human tissue factor (TF, Innovin) is from Siemens Healthcare Diagnostics (Puteaux, France). The thrombin calibrator, FluCaKit and round-bottomed 96-well microtiter plates (Immulon 2HB, plate with U-shaped bottom) from Diagnostics Stago (Asnières, France) were used for the thrombin generation tests. For the enzyme experiments, flat-bottomed 96-well microtiter plates were from Greiner (Frickenhausen, Germany); sheep anti-TFPI antibodies are from Affinity Biologicals (Sandhill Drive, Canada). The Actichrom assay of TFPI activity from American Diagnostica (Stamford, USA) was used for determining TFPI activity. The antithrombin activity assay (STA-Stachrom antithrombin III) is from Diagnostica STAGO. Enzymatic calculations were performed with PRISM 5.0.

Methods

1) Thrombin Generation Assay (TGA)

Measurements of thrombin generation were carried out by Hemker's method using 1 pM of Tissue Factor (TF) for activating coagulation and in the presence of 30 μg/ml CTI for inhibiting activation of the contact phase of coagulation during the incubation period (van Veen J J, Gatt A, Cooper P C, Kitchen S, Bowyer A E, Makris M. Corn trypsin inhibitor in fluorogenic thrombin-generation measurements is only necessary at low tissue factor concentrations and influences the relationship between factor VIII coagulant activity and thrombogram parameters. Blood Coagul Fibrinolysis. 2008 April; 19(3): 183-9). Briefly, a mixture of 20 µl of TF, 4 µM phospholipids, and 80 µl of plasma were pipetted in triplicate in a microtiter plate. Twenty microliters of Thrombin calibrator with 80 µl of plasma were also deposited by pipette in triplicate in the plate. The plate was then inserted in a Varioskan (Thermofisher, Illkirch, France) with an excitation wavelength set at 390 nm, with an emission wavelength of 460 nm and a pass band of 10 nm. Twenty microliters of FluCaKit (2.5 fluorogenic substrate mM (Z-Gly-Gly-Arg-AMC, ZGGR-AMC) with 0.1 M of $CaCl_2$) were injected into all the wells, thus starting the reaction. The fluorescence signal is read every 20 seconds for 60 min. The raw data on fluorescence intensities were exported to Sigmaplot® 9.0 for mathematical calculations using the 3-wave method described previously (De Smedt E. Advanced thrombinoscopy: PhD thesis, University Maastricht; 2007).

Hereinafter:

ETP denotes endogenous thrombin potential and corresponds to the area under curve;

PH denotes peak height and corresponds to the peak thrombin level;

LT is the latency time and corresponds to the time to reach 2 nM of thrombin;

PT is the peak time and corresponds to the time to obtain the PH.

The various factors GDXa, Xa or Novoseven® are diluted in buffer A comprising 1% Prionex, 18 mM of HEPES, 135 mM of sodium chloride, pH 7.35 and added to hemophiliac plasmas pretreated with CTI at various concentrations.

2) Neutralization of Antithrombin and TFPI by Specific Antibodies

For neutralization of antithrombin, a severe hemophilia A plasma was enriched with different concentrations of sheep IgG anti-human antithrombin antibody (1.8, 3, 5, and 7.5 g/l) and incubated for one hour at 25° C. before being tested in TGA. In parallel, the antithrombin activity was measured on a STAR coagulometer (Diagnostica Stago) with antithrombin III STA-Stachrom reagents.

For neutralization of TFPI, the same hemophilia A plasma was put in contact with different concentrations of sheep anti-human TFPI immunoglobulins (2.5, 5, 10 and 50 mg/l) before being tested in TGA. In parallel, the activity of the TFPI was determined with the Actichrom TFPI activity assay according to the manufacturer's instructions. Briefly, 20 µl of plasma diluted 20 times was incubated at 37° C. in the presence of 20 µl TF/FVIIa for 30 min. Then factor X (FX) was added and the whole was incubated at 37° C. for 15 min before adding EDTA and Spectrozyme FXa. The reaction was stopped 5 min later by adding glacial acetic acid and the absorbance was read at 405 nm.

3) Determinations of Chromogens 3.1) Determination of the Kinetic Constants of GDXa and Xa For determining GDXa or FXa activity, 0.3 nM of enzyme is incubated for 5 min at 37° C. in a buffer comprising 1% Prionex, 18 mM of HEPES, 135 mM of sodium chloride, pH 8.4. Then the chromogenic substrate PNAPEP 1025 is added at concentrations of 0.33, 0.50, 1, 1.5, and 2.0 mM, and the variation of absorbance is recorded at 405 nm.

3.2) Enzymatic Inhibition of Antithrombin (AT)

Xa or GDXa (1.25 nM) is incubated at 37° C. in buffer A in the presence of increasing concentrations of antithrombin (0 to 500 nM). Aliquots of 200 microliters of the mixture are taken at different time intervals, up to 90 min. Then 50 µl of chromogenic substrate PNAPEP 1025-6 mM is added and the change in absorbance is recorded.

3.3) Enzymatic Inhibition of TFPI

Inhibition of the activity of GDXa or FXa by TFPI was analyzed by incubating the enzyme at 0.25 nM for 3 h at 25° C. in buffer A in the presence of increasing concentrations of TFPI (from 0 to 30 nM for GDXa and from 0 to 10 nM for FXa) in a final volume of 200 µl. Then 50 µl of chromogenic substrate PNAPEP 1025 2.5 mM was added, and the change in absorbance was recorded. Ki* was determined as described previously (Bunce M W, Toso R, Camire R M. Zymogen-like factor Xa variants restore thrombin generation and effectively bypass the intrinsic pathway in vitro. Blood. 2011 Jan. 6; 117(1): 290-8; Baugh R J, Broze G J, Jr., Krishnaswamy S. Regulation of extrinsic pathway factor Xa formation by tissue factor pathway inhibitor. J Biol Chem. 1998; 273(8): 4378-86).

3.4) Determination of the Plasma Half-Life of GDXa and Xa

The plasma half-life of GDXa or Xa was determined by adding normal plasma with 50 nM of GDXa or of Xa. The mixture was then incubated at 37° C. Aliquots were taken from 0 to 60 min and immediately diluted 25 times in buffer A before adding the chromogenic substrate PNAPEP 1025 1.5 mM and determination of residual amidolytic activity, as described previously.

Example 2

Preparation of Modified Factor Xa

The plasmid pTT5 is opened by digestion with HindIII—BamHI enzymes and the genes coding for the signal peptide of TIMP1 with the HindIII and NheI restriction sites and FX lacking the Gla domain with the NheI and BamHI restriction sites are inserted, generating the plasmid pTT5-TIMX (pTT5 spTIMP1 gla less FX). The sequence coding for FX lacking the Gla domain according to the invention with the NheI and BamHI restriction sites was obtained by chemical synthesis (GenScript Corporation). Then a recognition site for furins was introduced upstream of the N-terminal isoleucine of the heavy chain permitting secretion of GDXa directly in the culture medium for purification. The GDXa produced is represented by the sequence identifier SEQ ID No. 3 for its light chain and by SEQ ID No. 2 for its heavy chain.

Example 3

Determination of the Kinetic Parameters of GDXa and FXa

Before analyzing the effect of GDXa on thrombin generation, the GDXa and Fxa were characterized using cleavage of the chromogenic substrate PNAPEP 1025. GDXa showed a similar affinity (Km=0.75±0.05 mM) to FXa (Km=0.64±0.03 mM) and similar catalytic properties: kcat=290±5 s−1 for GDXa and kcat=375±8 s−1 for FXa (Table 1). These results are consistent with the earlier observations obtained with a chromogenic substrate S2222 (Skogen W F, Esmon C T, Cox A C. Comparison of coagulation factor Xa and des-(1-44)factor Xa in the assembly of prothrombinase. J Biol Chem. 1984; 259(4): 2306-10).

TABLE 1 enzymatic properties of GDXa and FXa

|  | Km (mM) | kcat (s-1) | Antithrombin k2 ± SD (10 3.M-1.s-1) | TFPI Ki* ± SD (nM) |
|---|---|---|---|---|
| Xa | 0.65 ± | 368 ± | 1.50 ± 0.04 | 0.17 ± 0.031 |
| GDXa | 0.71 ± | 269 ± | 1.57 ± 0.08 | 0.31 ± 0.04 |

The results shown correspond to 2 independent measurements performed in triplicate using the chromogenic substrate PNAPEP 1025.

Example 4

Influence of GDXa or FXa on Thrombin Generation

At a concentration of 1 pM, TF is incapable of inducing production of thrombin in severe hemophiliac plasma A, as shown by the dotted line in FIG. 1A. However, in the presence of 50 pM GDXa, clear restoration of thrombin generation was observed (FIG. 1B). GDXa normalizes all the parameters associated with thrombin generation, including the endogenous thrombin potential (ETP), latency time, peak height, and peak time (FIG. 1B, Table 4). The thrombin generation observed was not a direct effect of GDXa on the plasma, as no thrombin was generated in the absence of TF (FIG. 1B, dotted line). This was observed in all the hemophiliac plasmas tested. Moreover, in contrast to GDXa, FXa triggered thrombin generation, even in the absence of TF (FIG. 1 C), as it is directly capable of converting prothrombin to thrombin.

To quantify possible interference by direct cleavage of the substrate ZGGR-AMC by GDXa, increasing amounts of enzyme were added in the presence of a saturating amount (6 µg/ml) of lepirudin (thrombin inhibitor). As shown in FIG. 1D, the raw fluorescence signal was completely cancelled in the presence of lepirudin. In these conditions, GDXa cleaved the substrate ZGGR-AMC in proportion to its concentration. At a concentration of 50 nM, the final signal corresponded to 8% of the fluorescence generated in the absence of lepirudin; at a concentration of 250 nM, the signal represented about 40% of the total fluorescence. However, because the signal is linear, it was included mathematically in the signal of the complex α2-macroglobulin-thrombin in the 3-wave method used for calculating the curves of thrombin concentration and does not affect the results of thrombin generation (De Smedt E. Advanced thrombinoscopy: PhD thesis, University Maastricht; 2007).

The minimum amount of GDXa capable of restoring thrombin generation in the plasma of patients with severe hemophilia A was evaluated. A concentration of 20 nM GDXa gave a curve of thrombin generation in this plasma (FIG. 1E) similar to that observed for normal plasma (FIG. 1A). Moreover, 10 nM GDXa generated a slightly higher signal than that obtained in the presence of 200 nM of rFVIIa (FIG. 1F).

Example 5

Effect of Anti-Antithrombin and Anti-TFPI Antibodies on Thrombin Generation

Figure 2:
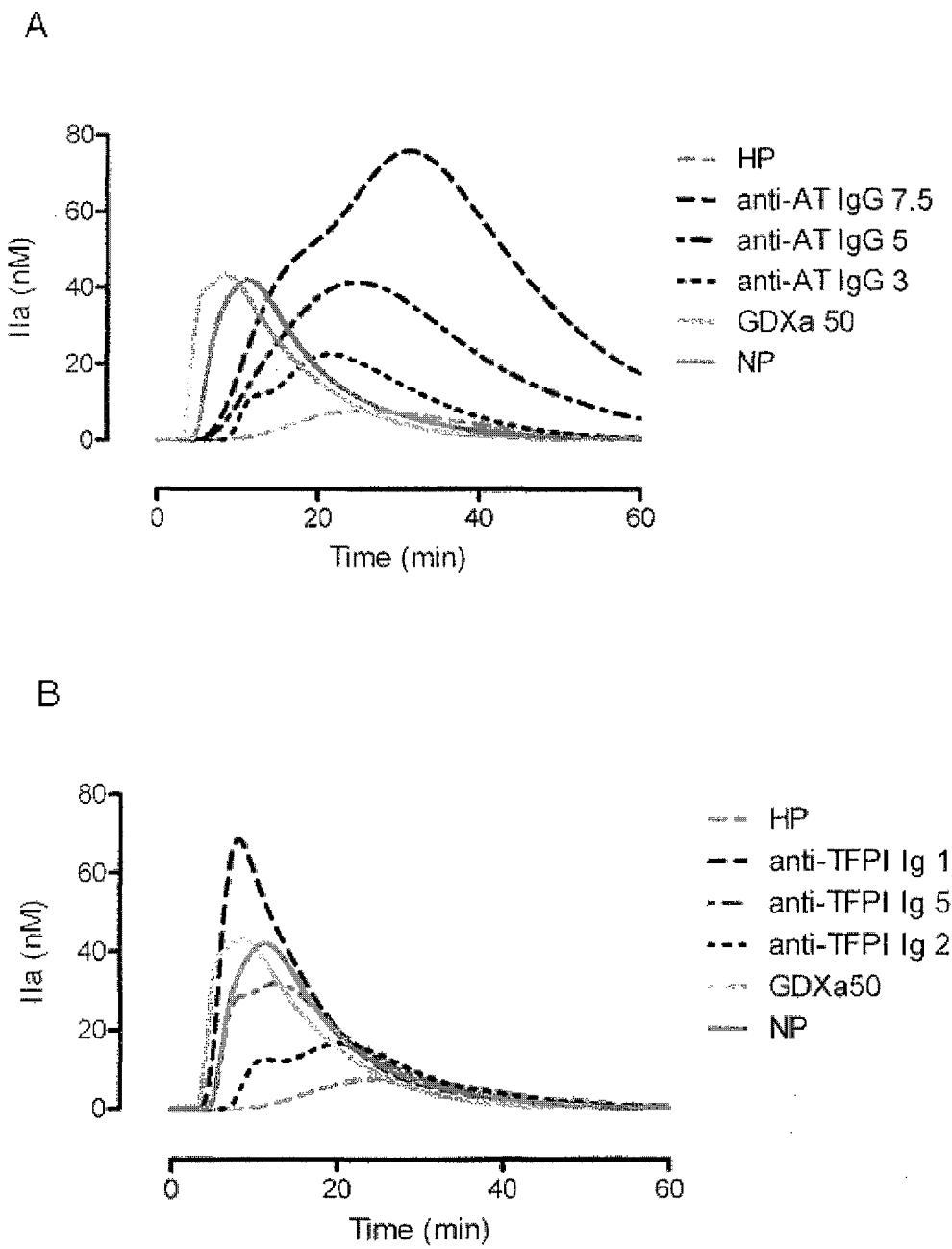
Figure 3:
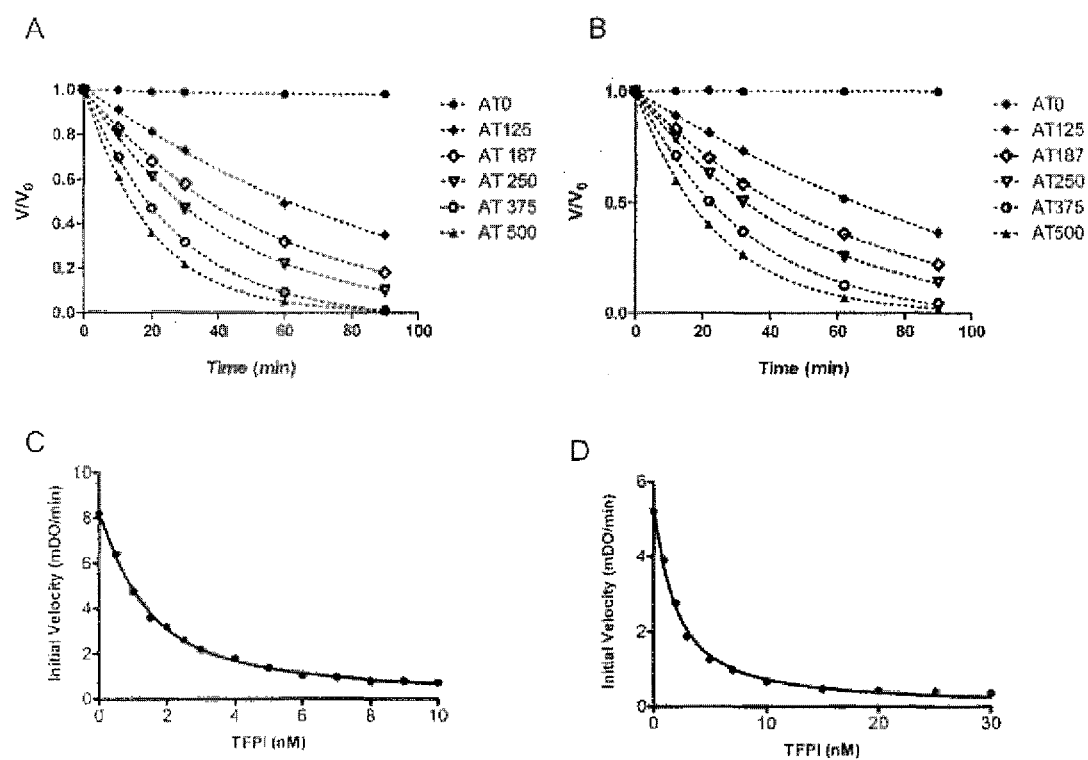

The anti-antithrombin antibody is able to massively increase ETP with little impact on the kinetic parameters (Table 2 and FIG. 2A). At 7.5 g/l of anti-antithrombin antibody (residual antithrombin activity 9%), ETP climbed to 2716 nM·min and PH reached 76 nM. This contrasts with the effect on the kinetic parameters (LT=6.6 min, PT=31.3 min). Moreover, as indicated previously by Erhardtsen et al. (Blocking of tissue factor pathway inhibitor (TFPI) shortens the bleeding time in rabbits with antibody induced hemophilia A. Blood Coagul Fibrinolysis. 1995; 6(5): 388-94), an anti-TFPI antibody was also able to restore coagulation in a hemophiliac plasma. At concentrations above 10 mg/l of anti-TFPI antibody (residual TFPI activity<30%), all the TGA parameters were corrected in this hemophilia plasma (Table 2). At 10 mg/l (Table 2 and FIG. 2B), ETP and PH increased from 209 to 762 nM·min and from 8 to 79 nM respectively. LT and PT decreased from 13.6 to 3.5 min and from 25.9 to 7.2 min respectively.

TABLE 2

Influence of antithrombin and anti-TFPI antibodies on thrombin generation

|  | NP | HP | GDXa 50 nM |
|---|---|---|---|
| AT activity (%) | — | 97 | — |
| TFPI activity (%) | — | 98 | — |
| ETP (nM.min-1) | 643 | 209 | 629 |
| PH (nM) | 42 | 7.7 | 43 |
| LT (min) | 4.9 | 13.6 | 3.4 |
| PT (min) | 11.3 | 25.9 | 8.6 |

| anti-AT IgG concentration (g/l) | anti-AT IgG 7.5 | anti-AT IgG 5 | anti-AT IgG 3 | anti-AT IgG 1.8 |
|---|---|---|---|---|
| AT residual activity (%) | 9 | 24 | 47 | 66 |
| ETP (nM.min-1) | 2716 | 1279 | 502 | 360 |
| PH (nM) | 76 | 41.4 | 22.5 | 15.5 |
| LT (min) | 6.6 | 7.2 | 9.4 | 9.8 |
| PT (min) | 31.3 | 24.8 | 21.5 | 23.8 |

| anti-TFPI Ig concentration (mg/l) | anti-TFPI Ig 50 | anti-TFPI Ig 10 | anti-TFPI Ig 5 | anti-TFPI Ig 2.5 |
|---|---|---|---|---|
| TFPI residual activity (%) | <20 | 29 | 53 | 80 |
| ETP (nM.min-1) | 732 | 762 | 593 | 383 |
| PH (nM) | 69.5 | 78.8 | 31.9 | 16.5 |
| LT (min) | 3.5 | 3.5 | 5 | 7.7 |
| PT (min) | 7.5 | 7.2 | 12.7 | 20.3 |

Various concentrations of human antithrombin antibody or anti-human TFPI antibodies were added to the plasmas of patients with severe hemophilia A prior to the thrombin generation assay.

HP: hemophiliac plasma;

NP: normal plasma.

The antithrombin and TFPI residual activities were measured according to the method described in the materials and methods.

GDXa: hemophiliac plasma with 50 nM GDXa.

The concentrations of anti-AT IgG are expressed in g/l.

The concentrations of anti-TFPI antibody are expressed in mg/l.

Example 6

Enzymatic Inhibition of GDXa and FXa by TFPI and Antithrombin

For irreversible enzymatic inhibition by antithrombin, the profiles of inhibition of GDXa ($1.50\pm0.04\times10^3$ $M^{-1}\cdot s^{-1}$, FIG. 2B) and of Xa were identical ($k_2=1.57\pm0.08\times10^3$ $M^{-1}\cdot s^{-1}$, FIG. 2A). TFPI is an inhibitor of slow fixation of FXa (26, 27) and, at a low concentration, a weak inhibitor of GDXa (28-30). Consequently, the inhibition of FXa and of GDXa were compared (Table 1). GDXa showed a lower affinity for TFPI (Ki*=$0.31\pm0.04$ nM, FIG. 2D) relative to FXa (Ki*=$0.17\pm0.03$ nM, FIG. 2C). Moreover, attainment of equilibrium in this experiment was suggested by the identity of the titration curves after incubation for 18 hours.

Example 7

Plasma Half-Life of GDXa and Xa

Figure 4:
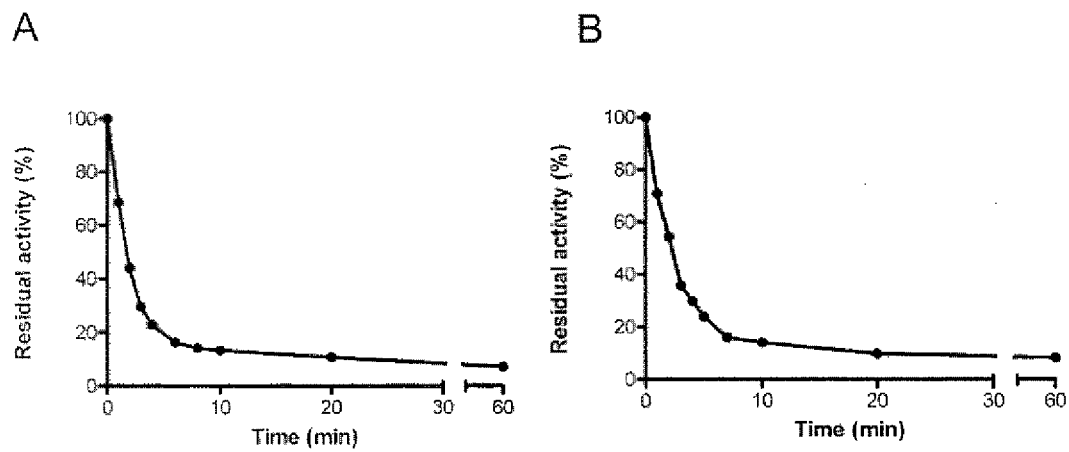

Considering the inhibition of GDXa by TFPI and antithrombin, the residual activity after adding 50 nM of GDXa or of FXa in the plasma at 37° C. was evaluated. As shown in FIG. 4A, the activity in the plasma decreased rapidly, a half-life of about 1 min 30 s was observed, and reached a plateau after 20 min for GDXa or FXa as previously indicated for FXa (Bunce M W, Toso R, Camire R M. Zymogen-like factor Xa variants restore thrombin generation and effectively bypass the intrinsic pathway in vitro. Blood. 2011 Jan. 6; 117(1): 290-8). Nevertheless, the effect on thrombin generation was maintained with the passage of time, such as at one hour, when the residual activity of GDXa was about 10% of its initial activity (FIG. 4B), restoration of thrombin generation was maintained. After incubation for 1 min, ETP increased from 0 to 610 nM and was still 478 nm after 60 min (Table 3). A similar correction was also observed for the maximum peak height (75 nM and 38 nM at 1 and 60 min, respectively) as well as for the shift and the peak times (Table 3).

TABLE 3

Effect of GDXa after 1 minute and 1 hour of incubation at 37° C. on a severe hemophiliac plasma

|  | 1 min | 60 min |
|---|---|---|
| ETP (nM.min) | 610 | 478 |
| PH (nM) | 75 | 38 |
| PT (s) | 6.6 | 8.8 |
| LT (s) | 1.4 | 2.1 |

50 nM of GDXa was added to a severe hemophiliac plasma A and was incubated at 37° C. for 1 hour. Aliquots were taken immediately and after 1 hour for measuring thrombin generation.

Example 8

Influence of GDXa on Thrombin Generation in Patients with Severe Hemophilia A with and without Inhibitor and in Patients with Severe Hemophilia B Thrombin generation was evaluated in plasma samples from five different donors with severe hemophilia A, including one donor with an inhibitor titrated at 50 Bethesda units, and of a plasma from a patient with severe hemophilia B. Thrombin generation was almost undetectable in the six plasmas when coagulation was triggered by 1 pM of TF, whereas it was restored in the presence of 20 and 50 nM GDXa. Table 4 shows that the corrections were observed at various degrees, for all the plasmas and for all the parameters associated with thrombin generation. In the presence of 20 nM GDXa, the ETP observed was 374±128 nM and the PH was 22±11 nM. LT and PT decreased by 5.0±1.5 and 13.9±3.8 min respectively.

Moreover, a dose effect was observed, the values increased to 533±132 nM for ETP and 46±20 nM for PH when 50 nM GDXa was added. LT and PT decreased by 2.8±0.7 and 9.2±2.7 min respectively.

TABLE 4

Influence of GDXa on thrombin generation on 5 different plasmas from patients with severe hemophilia A with or without inhibitor and of a plasma from a patient with severe hemophilia B

| ETP (nM.min) | GDXa 0 nM | GDXa 20 nM | GDXa 50 nM |
|---|---|---|---|
| NP | 611 | — | — |
| P1 (HA) | 0 | 536 | 530 |
| P2 (HA) | 0 | 268 | 420 |
| P3 (HA) | 0 | 207 | 330 |
| P4 (HA) | 0 | 466 | 610 |
| P5 (HA) | 215 | 331 | 629 |
| P6 (HA + I) | 254 | 425 | 539 |
| P7 (HB) | 282 | 546 | 668 |
| Mean ± SD | 125 ± 139 | 374 ± 128 | 533 ± 132 |

| PH (nM) | GDXa 0 nM | GDXa 20 nM | GDXa 50 nM |
|---|---|---|---|
| NP | 43 | ND | ND |
| P1 (HA) | 0 | 33 | 40 |
| P2 (HA) | 0 | 15 | 26 |
| P3 (HA) | 0 | 13 | 25 |
| P4 (HA) | 0 | 41 | 78 |
| P5 (HA) | 8 | 14 | 43 |
| P6 (HA + I) | 15 | 28 | 55 |
| P7 (HB) | 13 | 23 | 46 |
| Mean ± SD | 6 ± 7 | 22 ± 11 | 46 ± 20 |

| LT (min) | HP | GDXa 20 nM | GDXa 50 nM |
|---|---|---|---|
| NP | 5.7 | ND | ND |
| P1 (HA) | 0 | 3.1 | 2.3 |
| P2 (HA) | ND | 5.7 | 3.0 |
| P3 (HA) | ND | 4.5 | 2.9 |
| P4 (HA) | ND | 2.7 | 1.6 |
| P5 (HA) | 16 | 7.3 | 3.4 |
| P6 (HA + I) | 8 | 4.5 | 2.5 |
| P7 (HB) | 17 | 5.5 | 3.3 |
| Mean ± SD | ND | 5.0 ± 1.5 | 2.8 ± 0.7 |

| PT (min) | GDXa 0 nM | GDXa 20 nM | GDXa 50 nM |
|---|---|---|---|
| NP | 12.3 | ND | ND |
| P1 (HA) | 0 | 13.3 | 11.1 |
| P2 (HA) | ND | 17.6 | 14.1 |
| P3 (HA) | ND | 12.9 | 10.4 |
| P4 (HA) | ND | 8.6 | 7.3 |
| P5 (HA) | 30.3 | 18.9 | 8.6 |
| P6 (HA + I) | 24.4 | 12.4 | 7.4 |
| P7 (HB) | 28.9 | 12.8 | 7.3 |
| Mean ± SD | ND | 13.9 ± 3.8 | 9.2 ± 2.7 |

20 or 20 nM of GDXa was added to the various plasmas immediately assayed for thrombin generation.

Px: plasma x
HA: hemophilia A
HA+I: hemophilia A with inhibitor (hemophilia A with 50 BU of inhibitor)
HB: hemophilia B

Example 9

Figure 5:
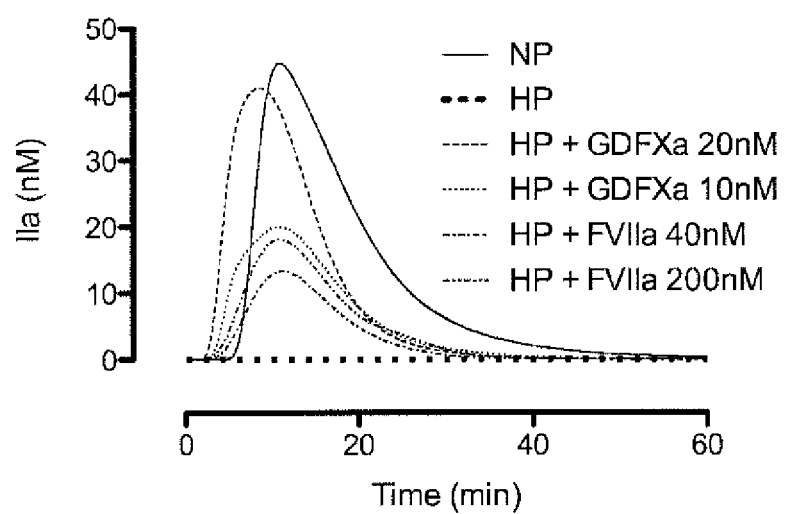

Comparison Between GDFXa and factor VIIa (rVIIa, Novoseven®) According to the Invention on Thrombin Generation in Subjects with Hemophilia A FIG. 5 shows that GDXa is much more effective than rVIIa (Novoseven®) for correcting thrombin generation.

At least 500 nM of rVIIa is required for correction according to: ALJAMALI M N, KJALKE M, HEDNER U, EZBAN M, TRANHOLM M. Thrombin generation and platelet activation induced by rFVIIa (NovoSeven®) and NN1731 in a reconstituted cell-based model mimicking hemophilia conditions. *Haemophilia*. 2009; 15: 1318-26.

The invention claimed is:

1. A method of treating a patient with hemophilia A or B comprising administering to the patient a pharmaceutical composition comprising:
    a modified factor Xa (GDXa); and
    a pharmaceutically acceptable carrier,
    wherein the GDXa comprises:
        a light chain consisting of the amino acid sequence set forth in SEQ ID NO: 3, and
        a heavy chain consisting of the amino acid sequence set forth in SEQ ID NO: 2; wherein the GDXa does not comprise amino acid residues 1-43 of SEQ ID NO:1.

2. The method according to claim 1, wherein the GDXa is administered at a dose of 4.5 to 27 µg/kg by the systemic, nasal or parenteral administration to the patient.

3. The method according to claim 1, wherein the method treats a hemorrhagic syndrome in the patient.

4. The method according to claim 1, wherein the method treats a hemorrhagic accident in the patient.

* * * * *

SEQUENCE LISTING

<160> NUMBER OF SEQ ID NOS: 28

<210> SEQ ID NO 1
<211> LENGTH: 142
<212> TYPE: PRT
<213> ORGANISM: Homo sapiens

<400> SEQUENCE: 1

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg
    130                 135                 140

<210> SEQ ID NO 2
<211> LENGTH: 254
<212> TYPE: PRT
<213> ORGANISM: Homo sapiens

<400> SEQUENCE: 2

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg

```
                180                 185                 190
Phe Lys Asp Thr Tyr Phe Val Thr Gly Ile Val Ser Trp Gly Glu Gly
            195                 200                 205

Cys Ala Arg Lys Gly Lys Tyr Gly Ile Tyr Thr Lys Val Thr Ala Phe
        210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 3
<211> LENGTH: 98
<212> TYPE: PRT
<213> ORGANISM: Homo sapiens

<400> SEQUENCE: 3

Lys Asp Gly Asp Gln Cys Glu Thr Ser Pro Cys Gln Asn Gln Gly Lys
1               5                   10                  15

Cys Lys Asp Gly Leu Gly Glu Tyr Thr Cys Thr Cys Leu Glu Gly Phe
            20                  25                  30

Glu Gly Lys Asn Cys Glu Leu Phe Thr Arg Lys Leu Cys Ser Leu Asp
        35                  40                  45

Asn Gly Asp Cys Asp Gln Phe Cys His Glu Glu Gln Asn Ser Val Val
    50                  55                  60

Cys Ser Cys Ala Arg Gly Tyr Thr Leu Ala Asp Asn Gly Lys Ala Cys
65                  70                  75                  80

Ile Pro Thr Gly Pro Tyr Pro Cys Gly Lys Gln Thr Leu Glu Arg Arg
                85                  90                  95

Lys Arg

<210> SEQ ID NO 4
<211> LENGTH: 59
<212> TYPE: PRT
<213> ORGANISM: Homo sapiens

<400> SEQUENCE: 4

Phe Thr Arg Lys Leu Cys Ser Leu Asp Asn Gly Asp Cys Asp Gln Phe
1               5                   10                  15

Cys His Glu Glu Gln Asn Ser Val Val Cys Ser Cys Ala Arg Gly Tyr
            20                  25                  30

Thr Leu Ala Asp Asn Gly Lys Ala Cys Ile Pro Thr Gly Pro Tyr Pro
        35                  40                  45

Cys Gly Lys Gln Thr Leu Glu Arg Arg Lys Arg
    50                  55

<210> SEQ ID NO 5
<211> LENGTH: 57
<212> TYPE: PRT
<213> ORGANISM: Homo sapiens

<400> SEQUENCE: 5

Lys Asp Gly Asp Gln Cys Glu Thr Ser Pro Cys Gln Asn Gln Gly Lys
1               5                   10                  15

Cys Lys Asp Gly Leu Gly Glu Tyr Thr Cys Thr Cys Leu Glu Gly Phe
            20                  25                  30

Glu Gly Lys Asn Cys Glu Leu Phe Pro Thr Gly Pro Tyr Pro Cys Gly
        35                  40                  45
```

```
Lys Gln Thr Leu Glu Arg Arg Lys Arg
    50                  55

<210> SEQ ID NO 6
<211> LENGTH: 17
<212> TYPE: PRT
<213> ORGANISM: Homo sapiens

<400> SEQUENCE: 6

Pro Thr Gly Pro Tyr Pro Cys Gly Lys Gln Thr Leu Glu Arg Arg Lys
1               5                   10                  15

Arg

<210> SEQ ID NO 7
<211> LENGTH: 353
<212> TYPE: PRT
<213> ORGANISM: Homo sapiens

<400> SEQUENCE: 7

Tyr Lys Asp Gly Asp Gln Cys Glu Thr Ser Pro Cys Gln Asn Gln Gly
1               5                   10                  15

Lys Cys Lys Asp Gly Leu Gly Glu Tyr Thr Cys Thr Cys Leu Glu Gly
            20                  25                  30

Phe Glu Gly Lys Asn Cys Glu Leu Phe Thr Arg Lys Leu Cys Ser Leu
        35                  40                  45

Asp Asn Gly Asp Cys Asp Gln Phe Cys His Glu Glu Gln Asn Ser Val
    50                  55                  60

Val Cys Ser Cys Ala Arg Gly Tyr Thr Leu Ala Asp Asn Gly Lys Ala
65                  70                  75                  80

Cys Ile Pro Thr Gly Pro Tyr Pro Cys Gly Lys Gln Thr Leu Glu Arg
                85                  90                  95

Arg Lys Arg Ile Val Gly Gly Gln Glu Cys Lys Asp Gly Glu Cys Pro
            100                 105                 110

Trp Gln Ala Leu Leu Ile Asn Glu Glu Asn Glu Gly Phe Cys Gly Gly
        115                 120                 125

Thr Ile Leu Ser Glu Phe Tyr Ile Leu Thr Ala Ala His Cys Leu Tyr
    130                 135                 140

Gln Ala Lys Arg Phe Lys Val Arg Val Gly Asp Arg Asn Thr Glu Gln
145                 150                 155                 160

Glu Glu Gly Gly Glu Ala Val His Glu Val Glu Val Ile Lys His
                165                 170                 175

Asn Arg Phe Thr Lys Glu Thr Tyr Asp Phe Asp Ile Ala Val Leu Arg
            180                 185                 190

Leu Lys Thr Pro Ile Thr Phe Arg Met Asn Val Ala Pro Ala Cys Leu
        195                 200                 205

Pro Glu Arg Asp Trp Ala Glu Ser Thr Leu Met Thr Gln Lys Thr Gly
    210                 215                 220

Ile Val Ser Gly Phe Gly Arg Thr His Glu Lys Gly Arg Gln Ser Thr
225                 230                 235                 240

Arg Leu Lys Met Leu Glu Val Pro Tyr Val Asp Arg Asn Ser Cys Lys
                245                 250                 255

Leu Ser Ser Ser Phe Ile Ile Thr Gln Asn Met Phe Cys Ala Gly Tyr
            260                 265                 270

Asp Thr Lys Gln Glu Asp Ala Cys Gln Gly Asp Ser Gly Gly Pro His
        275                 280                 285

Val Thr Arg Phe Lys Asp Thr Tyr Phe Val Thr Gly Ile Val Ser Trp
```

```
                    290                 295                 300
Gly Glu Gly Cys Ala Arg Lys Gly Lys Tyr Gly Ile Tyr Thr Lys Val
305                 310                 315                 320

Thr Ala Phe Leu Lys Trp Ile Asp Arg Ser Met Lys Thr Arg Gly Leu
                325                 330                 335

Pro Lys Ala Lys Ser His Ala Pro Glu Val Ile Thr Ser Ser Pro Leu
                340                 345                 350

Lys

<210> SEQ ID NO 8
<211> LENGTH: 1059
<212> TYPE: DNA
<213> ORGANISM: Homo sapiens

<400> SEQUENCE: 8
tacaaagatg gcgaccagtg tgagaccagt ccttgccaga accagggcaa atgtaaagac      60
ggcctcgggg aatacacctg cacctgttta gaaggattcg aaggcaaaaa ctgtgaatta    120
ttcacacgga agctctgcag cctggacaac ggggactgtg accagttctg ccacgaggaa    180
cagaactctg tggtgtgctc ctgcgcccgc gggtacaccc tggctgacaa cggcaaggcc    240
tgcattccca cagggcccta cccctgtggg aaacagaccc tggaacgcag gaagaggatc    300
gtgggaggcc aggaatgcaa ggacggggag tgtccctggc aggccctgct catcaatgag    360
gaaaacgagg gtttctgtgg tggaaccatt ctgagcgagt tctacatcct aacggcagcc    420
cactgtctct accaagccaa gagattcaag gtgagggtag ggaccggaa cacggagcag    480 gaggagggcg gtgaggcggt gcacgaggtg gaggtggtca tcaagcacaa ccggttcaca    540
aaggagacct atgacttcga catcgccgtg ctccggctca agacccccat caccttccgc    600
atgaacgtgg cgcctgcctg cctccccgag cgtgactggg ccgagtccac gctgatgacg    660
cagaagacgg ggattgtgag cggcttcggg cgcacccacg agaagggccg gcagtccacc    720
aggctcaaga tgctggaggt gcccctacgt gaccgcaaca gctgcaagct gtccagcagc    780
ttcatcatca cccagaacat gttctgtgcc ggctacgaca ccaagcagga ggatgcctgc    840 caggggggaca gcgggggccc gcacgtcacc cgcttcaagg acacctactt cgtgacaggc    900
atcgtcagct ggggagaggg ctgtgcccgt aaggggaagt acgggatcta caccaaggtc    960
accgccttcc tcaagtggat cgacaggtcc atgaaaacca ggggcttgcc caaggccaag   1020
agccatgccc cggaggtcat aacgtcctct ccattaaag                           1059

<210> SEQ ID NO 9
<211> LENGTH: 254
<212> TYPE: PRT
<213> ORGANISM: Homo sapiens

<400> SEQUENCE: 9

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80
```

```
Thr Tyr Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 10
<211> LENGTH: 254
<212> TYPE: PRT
<213> ORGANISM: Homo sapiens

<400> SEQUENCE: 10

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
                20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
        50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Phe Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
```

```
                195                 200                 205
Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 11
<211> LENGTH: 254
<212> TYPE: PRT
<213> ORGANISM: Homo sapiens

<400> SEQUENCE: 11

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
                20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
    115                 120                 125

Gly Phe Gly Arg Thr His Glu Lys Gly Arg Gln Ser Thr Gly Leu Lys
130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
    195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 12
<211> LENGTH: 254
<212> TYPE: PRT
<213> ORGANISM: Homo sapiens

<400> SEQUENCE: 12

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
```

```
                20                  25                  30
Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
        50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Ile Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 13
<211> LENGTH: 254
<212> TYPE: PRT
<213> ORGANISM: Homo sapiens

<400> SEQUENCE: 13

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Tyr Leu Lys
    130                 135                 140
```

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
            165                 170                 175

Gln Glu Asp Ala Cys Gln Gly Asp Ser Gly Gly Pro His Val Thr Arg
        180                 185                 190

Phe Lys Asp Thr Tyr Phe Val Thr Gly Ile Val Ser Trp Gly Glu Gly
    195                 200                 205

Cys Ala Arg Lys Gly Lys Tyr Gly Ile Tyr Thr Lys Val Thr Ala Phe
        210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 14
<211> LENGTH: 426
<212> TYPE: DNA
<213> ORGANISM: Homo sapiens

<400> SEQUENCE: 14
gccaattcct ttcttgaaga gatgaagaaa ggacacctcg aaagagagtg catggaagag      60
acctgctcat acgaagaggc ccgcgaggtc tttgaggaca cgacaagac gaatgaattc     120 tggaataaat acaaagatgg cgaccagtgt gagaccagtc cttgccagaa ccagggcaaa    180
tgtaaagacg gcctcgggga atacacctgc acctgtttag aaggattcga aggcaaaaac    240
tgtgaattat tcacacggaa gctctgcagc ctggacaacg gggactgtga ccagttctgc    300
cacgaggaac agaactctgt ggtgtgctcc tgcgcccgcg gtacaccct ggctgacaac     360 ggcaaggcct gcattccac agggccctac ccctgtggga acagaccct ggaacgcagg      420 aagagg                                                                426

<210> SEQ ID NO 15
<211> LENGTH: 762
<212> TYPE: DNA
<213> ORGANISM: Homo sapiens

<400> SEQUENCE: 15
atcgtgggag gccaggaatg caaggacggg gagtgtccct gcaggcccct gctcatcaat     60
gaggaaaacg agggtttctg tggtggaacc attctgagcg agttctacat cctaacggca    120
gcccactgtc tctaccaagc caagagattc aaggtgaggg taggggaccg gaacacggag    180
caggaggagg gcggtgaggc ggtgcacgag gtggaggtgg tcatcaagca caaccggttc    240
acaaaggaga cctatgactt cgacatcgcc gtgctccggc tcaagacccc catcaccttc    300
cgcatgaacg tggcgcctgc ctgcctcccc gagcgtgact gggccgagtc cacgctgatg    360
acgcagaaga cggggattgt gagcggcttc ggcgcacccc acgagaaggg ccggcagtcc    420
accaggctca gatgctggag ggtgcccctac gtggaccgca cagctgcaa gctgtccagc    480 agcttcatca tcacccagaa catgttctgt gccggctacg acaccaagca ggaggatgcc    540 tgccagggg acagcggggg cccgcacgtc acccgcttca ggacaccta cttcgtgaca    600 ggcatcgtca gctggggaga gggctgtgcc cgtaagggga agtacgggat ctacaccaag    660
gtcaccgcct tcctcaagtg gatcgacagg tccatgaaaa ccaggggctt gcccaaggcc    720
aagagccatg ccccggaggt cataacgtcc tctccattaa ag                        762

<210> SEQ ID NO 16
<211> LENGTH: 297
<212> TYPE: DNA
<213> ORGANISM: Homo sapiens

<400> SEQUENCE: 16

```
tacaaagatg gcgaccagtg tgagaccagt ccttgccaga accagggcaa atgtaaagac      60
ggcctcgggg aatacacctg cacctgttta gaaggattcg aaggcaaaaa ctgtgaatta     120
ttcacacgga agctctgcag cctggacaac ggggactgtg accagttctg ccacgaggaa     180
cagaactctg tggtgtgctc ctgcgcccgc gggtacaccc tggctgacaa cggcaaggcc     240
tgcattccca cagggcccta cccctgtggg aaacagaccc tggaacgcag gaagagg        297
```

<210> SEQ ID NO 17
<211> LENGTH: 177
<212> TYPE: DNA
<213> ORGANISM: Homo sapiens

<400> SEQUENCE: 17

```
ttcacacgga agctctgcag cctggacaac ggggactgtg accagttctg ccacgaggaa      60
cagaactctg tggtgtgctc ctgcgcccgc gggtacaccc tggctgacaa cggcaaggcc     120
tgcattccca cagggcccta cccctgtggg aaacagaccc tggaacgcag gaagagg        177
```

<210> SEQ ID NO 18
<211> LENGTH: 171
<212> TYPE: DNA
<213> ORGANISM: Homo sapiens

<400> SEQUENCE: 18

```
aaagatggcg accagtgtga gaccagtcct tgccagaacc aggcaaatg taaagacggc       60
ctcggggaat acacctgcac ctgtttagaa ggattcgaag gcaaaaactg tgaattattc     120
cccacagggc cctaccctg tgggaaacag accctggaac gcaggaagag g               171
```

<210> SEQ ID NO 19
<211> LENGTH: 51
<212> TYPE: DNA
<213> ORGANISM: Homo sapiens

<400> SEQUENCE: 19

```
cccacagggc cctaccctg tgggaaacag accctggaac gcaggaagag g                51
```

<210> SEQ ID NO 20
<211> LENGTH: 1233
<212> TYPE: DNA
<213> ORGANISM: Homo sapiens

<400> SEQUENCE: 20

```
tacaaagatg gcgaccagtg tgagaccagt ccttgccaga accagggcaa atgtaaagac      60
ggcctcgggg aatacacctg cacctgttta gaaggattcg aaggcaaaaa ctgtgaatta     120
ttcacacgga agctctgcag cctggacaac ggggactgtg accagttctg ccacgaggaa     180
cagaactctg tggtgtgctc ctgcgcccgc gggtacaccc tggctgacaa cggcaaggcc     240
tgcattccca cagggcccta cccctgtggg aaacagaccc tggaacgcag gaagaggtca     300
gtggcccagg ccaccagcag cagcggggag gcccctgaca gcatcacatg gaagccatat     360
gatgcagccg acctggaccc caccgagaac cccttcgacc tgcttgactt caaccagacg     420
cagcctgaga ggggcgacaa caacctcacc aggaggaaga ggaggaagag gatcgtggga     480
```

-continued

```
ggccaggaat gcaaggacgg ggagtgtccc tggcaggccc tgctcatcaa tgaggaaaac      540 gagggttttct gtggtggaac cattctgagc gagttctaca tcctaacggc agcccactgt    600
ctctaccaag ccaagagatt caaggtgagg gtaggggacc ggaacacgga gcaggaggag     660
ggcggtgagg cggtgcacga ggtggaggtg gtcatcaagc acaaccggtt cacaaaggag    720
acctatgact tcgacatcgc cgtgctccgg ctcaagaccc ccatcacctt ccgcatgaac    780
gtggcgcctg cctgcctccc cgagcgtgac tgggccgagt ccacgctgat gacgcagaag    840
acggggattg tgagcggctt cgggcgcacc cacgagaagg gccggcagtc caccaggctc    900
aagatgctgg aggtgcccta cgtggaccgc aacagctgca agctgtccag cagcttcatc     960
atcacccaga acatgttctg tgccggctac gacaccaagc aggaggatgc ctgccagggg    1020
gacagcgggg gccgcacgt cacccgcttc aaggacacct acttcgtgac aggcatcgtc    1080
agctggggag agggctgtgc cgtaagggg aagtacggga tctacaccaa ggtcaccgcc     1140
ttcctcaagt ggatcgacag gtccatgaaa accaggggct gcccaaggc caagagccat    1200 gccccggagg tcataacgtc ctctccatta aag                                 1233
```

<210> SEQ ID NO 21
<211> LENGTH: 762
<212> TYPE: DNA
<213> ORGANISM: Homo sapiens

<400> SEQUENCE: 21

```
atcgtgggag gccaggaatg caaggacggg gagtgtccct ggcaggccct gctcatcaat     60
gaggaaaacg agggtttctg tggtggaacc attctgagcg agttctacat cctaacggca    120
gcccactgtc tctaccaagc caagagattc aaggtgaggg taggggaccg gaacacggag    180
caggaggagg gcggtgaggc ggtgcacgag gtggaggtgg tcatcaagca caaccggttc    240
acatacgaga cctatgactt cgacatcgcc gtgctccggc tcaagacccc catcaccttc    300
cgcatgaacg tggcgcctgc ctgcctcccc gagcgtgact gggccgagtc cacgctgatg    360
acgcagaaga cggggattgt gagcggcttg gggcgcaccc acgagaaggg ccggcagtcc    420
accaggctca agatgctgga ggtgccctac gtggaccgca acagctgcaa gctgtccagc    480
agcttcatca tcacccagaa catgttctgt gccggctacg acaccaagca ggaggatgcc    540
tgccaggggg acagcggggg cccgcacgtc acccgcttca aggacaccta cttcgtgaca    600
ggcatcgtca gctggggaga gggctgtgcc cgtaagggga agtacgggat ctacaccaag    660
gtcaccgcct tcctcaagtg gatcgacagg tccatgaaaa caggggcttg cccaaggcc    720 aagagccatg ccccggaggt cataacgtcc tctccattaa ag                        762
```

<210> SEQ ID NO 22
<211> LENGTH: 762
<212> TYPE: DNA
<213> ORGANISM: Homo sapiens

<400> SEQUENCE: 22

```
atcgtgggag gccaggaatg caaggacggg gagtgtccct ggcaggccct gctcatcaat     60
gaggaaaacg agggtttctg tggtggaacc attctgagcg agttctacat cctaacggca    120
gcccactgtc tctaccaagc caagagattc aaggtgaggg taggggaccg gaacacggag    180
caggaggagg gcggtgaggc ggtgcacgag gtggaggtgg tcatcaagca caaccggttc    240
acaaaggaga cctatgactt cgacatcgcc gtgctccggc tcaagacccc catcaccttc    300
```

```
cgcatgaacg tggcgcctgc ctgcctcccc gagcgtgact gggccgagtc cacgctgatg      360
acgcagaaga cggggattgt gagcggcttc gggcgcaccc acgagaaggg ccggcagtcc      420
accttcctca agatgctgga ggtgccctac gtggaccgca acagctgcaa gctgtccagc      480
agcttcatca tcacccagaa catgttctgt gccggctacg acaccaagca ggaggatgcc      540
tgccaggggg acagcggggg cccgcacgtc acccgcttca aggacaccta cttcgtgaca      600
ggcatcgtca gctggggaga gggctgtgcc cgtaagggga agtacgggat ctacaccaag      660
gtcaccgcct tcctcaagtg gatcgacagg tccatgaaaa ccaggggctt gcccaaggcc      720
aagagccatg ccccggaggt cataacgtcc tctccattaa ag                        762
```

<210> SEQ ID NO 23
<211> LENGTH: 762
<212> TYPE: DNA
<213> ORGANISM: Homo sapiens

<400> SEQUENCE: 23

```
atcgtgggag gccaggaatg caaggacggg gagtgtccct ggcaggccct gctcatcaat       60
gaggaaaacg agggtttctg tggtggaacc attctgagcg agttctacat cctaacggca      120
gcccactgtc tctaccaagc caagagattc aaggtgaggg taggggaccg gaacacggag      180
caggaggagg gcggtgaggc ggtgcacgag gtggaggtgg tcatcaagca caaccggttc      240
acaaaggaga cctatgactt cgacatcgcc gtgctccggc tcaagacccc catcaccttc      300
cgcatgaacg tggcgcctgc ctgcctcccc gagcgtgact gggccgagtc cacgctgatg      360
acgcagaaga cggggattgt gagcggcttc gggcgcaccc acgagaaggg ccggcagtcc      420
accggactca agatgctgga ggtgccctac gtggaccgca acagctgcaa gctgtccagc      480
agcttcatca tcacccagaa catgttctgt gccggctacg acaccaagca ggaggatgcc      540
tgccaggggg acagcggggg cccgcacgtc acccgcttca aggacaccta cttcgtgaca      600
ggcatcgtca gctggggaga gggctgtgcc cgtaagggga agtacgggat ctacaccaag      660
gtcaccgcct tcctcaagtg gatcgacagg tccatgaaaa ccaggggctt gcccaaggcc      720
aagagccatg ccccggaggt cataacgtcc tctccattaa ag                        762
```

<210> SEQ ID NO 24
<211> LENGTH: 762
<212> TYPE: DNA
<213> ORGANISM: Homo sapiens

<400> SEQUENCE: 24

```
atcgtgggag gccaggaatg caaggacggg gagtgtccct ggcaggccct gctcatcaat       60
gaggaaaacg agggtttctg tggtggaacc attctgagcg agttctacat cctaacggca      120
gcccactgtc tctaccaagc caagagattc aaggtgaggg taggggaccg gaacacggag      180
caggaggagg gcggtgaggc ggtgcacgag gtggaggtgg tcatcaagca caaccggttc      240
acaaaggaga cctatgactt cgacatcgcc gtgctccggc tcaagacccc catcaccttc      300
cgcatgaacg tggcgcctgc ctgcctcccc gagcgtgact gggccgagtc cacgctgatg      360
acgcagaaga cggggattgt gagcggcttc gggcgcaccc acgagaaggg ccggcagtcc      420
accatactca agatgctgga ggtgccctac gtggaccgca acagctgcaa gctgtccagc      480
agcttcatca tcacccagaa catgttctgt gccggctacg acaccaagca ggaggatgcc      540
tgccaggggg acagcggggg cccgcacgtc acccgcttca aggacaccta cttcgtgaca      600
ggcatcgtca gctggggaga gggctgtgcc cgtaagggga agtacgggat ctacaccaag      660
```
gtcaccgcct tcctcaagtg gatcgacagg tccatgaaaa ccaggggctt gcccaaggcc  720
aagagccatg ccccggaggt cataacgtcc tctccattaa ag  762

<210> SEQ ID NO 25
<211> LENGTH: 762
<212> TYPE: DNA
<213> ORGANISM: Homo sapiens

<400> SEQUENCE: 25
atcgtgggag gccaggaatg caaggacggg gagtgtccct ggcaggccct gctcatcaat  60
gaggaaaacg agggtttctg tggtggaacc attctgagcg agttctacat cctaacggca  120
gcccactgtc tctaccaagc caagagattc aaggtgaggg taggggaccg gaacacggag  180
caggaggagg gcggtgaggc ggtgcacgag gtggaggtgg tcatcaagca caaccggttc  240
acaaaggaga cctatgactt cgacatcgcc gtgctccggc tcaagacccc catcaccttc  300
cgcatgaacg tggcgcctgc ctgcctcccc gagcgtgact gggccgagtc cacgctgatg  360
acgcagaaga cggggattgt gagcggcttc gggcgcaccc acgagaaggg ccggcagtcc  420
acctacctca agatgctgga ggtgccctac gtggaccgca cagctgcaa gctgtccagc  480 agcttcatca tcacccagaa catgttctgt gccggctacg acaccaagca ggaggatgcc  540
tgccaggggg acagcggggg cccgcacgtc acccgcttca aggacaccta cttcgtgaca  600
ggcatcgtca gctggggaga gggctgtgcc cgtaagggga agtacgggat ctacaccaag  660
gtcaccgcct tcctcaagtg gatcgacagg tccatgaaaa ccaggggctt gcccaaggcc  720
aagagccatg ccccggaggt cataacgtcc tctccattaa ag  762

<210> SEQ ID NO 26
<211> LENGTH: 254
<212> TYPE: PRT
<213> ORGANISM: Bovide

<400> SEQUENCE: 26

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Leu Ser Ser Thr Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

```
Gln Glu Asp Ala Cys Gln Gly Asp Ser Gly Gly Pro His Val Thr Arg
                180                 185                 190
Phe Lys Asp Thr Tyr Phe Val Thr Gly Ile Val Ser Trp Gly Glu Gly
            195                 200                 205
Cys Ala Arg Lys Gly Lys Tyr Gly Ile Tyr Thr Lys Val Thr Ala Phe
        210                 215                 220
Leu Lys Trp Ile Asp Arg Ser Met Lys Thr Arg Gly Leu Pro Lys Ala
225                 230                 235                 240
Lys Ser His Ala Pro Glu Val Ile Thr Ser Ser Pro Leu Lys
                245                 250
```

<210> SEQ ID NO 27
<211> LENGTH: 765
<212> TYPE: DNA
<213> ORGANISM: Bovine

<400> SEQUENCE: 27

```
atcgtgggag gccaggaatg caaggacggg gagtgtccct ggcaggccct gctcatcaat      60
gaggaaaacg agggtttctg tggtggaacc attctgagcg agttctacat cctaacggca     120
gcccactgtc tctaccaagc caagagattc aaggtgaggg taggggaccg gaacacggag     180
caggaggagg gcggtgaggc ggtgcacgag gtggaggtgg tcatcaagca caaccggttc     240
acaaaggaga cctatgactt cgacatcgcc gtgctccggc tcaagacccc catcaccttc     300
cgcatgaacg tggcgcctgc ctgcctcccc gagcgtgact gggccgagtc cacgctgatg     360
acgcagaaga cggggattgt gagcggcttc gggcgcaccc acgagaaggg ccggctgtcc     420
tccacgctca gatgctggag gtgccctac gtggaccgca acagctgcaa gctgtccagc     480
agcttcatca tcacccagaa catgttctgt gccggctacg acaccaagca ggaggatgcc     540
tgccaggggg acagcggggg cccgcacgtc acccgcttca aggacaccta cttcgtgaca     600
ggcatcgtca gctggggaga gggctgtgcc cgtaagggga gtacgggat ctacaccaag     660
gtcaccgcct tcctcaagtg gatcgacagg tccatgaaaa ccaggggctt gcccaaggcc     720
aagagccatg ccccggaggt cataacgtcc tctccattaa agtga                     765
```

<210> SEQ ID NO 28
<211> LENGTH: 411
<212> TYPE: PRT
<213> ORGANISM: Homo sapiens

<400> SEQUENCE: 28

```
Tyr Lys Asp Gly Asp Gln Cys Glu Thr Ser Pro Cys Gln Asn Gln Gly
1               5                   10                  15
Lys Cys Lys Asp Gly Leu Gly Glu Tyr Thr Cys Thr Cys Leu Glu Gly
                20                  25                  30
Phe Glu Gly Lys Asn Cys Glu Leu Phe Thr Arg Lys Leu Cys Ser Leu
            35                  40                  45
Asp Asn Gly Asp Cys Asp Gln Phe Cys His Glu Glu Gln Asn Ser Val
        50                  55                  60
Val Cys Ser Cys Ala Arg Gly Tyr Thr Leu Ala Asp Asn Gly Lys Ala
65                  70                  75                  80
Cys Ile Pro Thr Gly Pro Tyr Pro Cys Gly Lys Gln Thr Leu Glu Arg
                85                  90                  95
Arg Lys Arg Ser Val Ala Gln Ala Thr Ser Ser Gly Glu Ala Pro
                100                 105                 110
```

-continued

```
Asp Ser Ile Thr Trp Lys Pro Tyr Asp Ala Ala Asp Leu Asp Pro Thr
        115                 120                 125

Glu Asn Pro Phe Asp Leu Leu Asp Phe Asn Gln Thr Gln Pro Glu Arg
        130                 135                 140

Gly Asp Asn Asn Leu Thr Arg Arg Lys Arg Arg Lys Arg Ile Val Gly
145                 150                 155                 160

Gly Gln Glu Cys Lys Asp Gly Glu Cys Pro Trp Gln Ala Leu Leu Ile
                165                 170                 175

Asn Glu Glu Asn Glu Gly Phe Cys Gly Gly Thr Ile Leu Ser Glu Phe
                180                 185                 190

Tyr Ile Leu Thr Ala Ala His Cys Leu Tyr Gln Ala Lys Arg Phe Lys
                195                 200                 205

Val Arg Val Gly Asp Arg Asn Thr Glu Gln Glu Glu Gly Gly Glu Ala
        210                 215                 220

Val His Glu Val Glu Val Val Ile Lys His Asn Arg Phe Thr Lys Glu
225                 230                 235                 240

Thr Tyr Asp Phe Asp Ile Ala Val Leu Arg Leu Lys Thr Pro Ile Thr
                245                 250                 255

Phe Arg Met Asn Val Ala Pro Ala Cys Leu Pro Glu Arg Asp Trp Ala
                260                 265                 270

Glu Ser Thr Leu Met Thr Gln Lys Thr Gly Ile Val Ser Gly Phe Gly
        275                 280                 285

Arg Thr His Glu Lys Gly Arg Gln Ser Thr Arg Leu Lys Met Leu Glu
        290                 295                 300

Val Pro Tyr Val Asp Arg Asn Ser Cys Lys Leu Ser Ser Ser Phe Ile
305                 310                 315                 320

Ile Thr Gln Asn Met Phe Cys Ala Gly Tyr Asp Thr Lys Gln Glu Asp
                325                 330                 335

Ala Cys Gln Gly Asp Ser Gly Gly Pro His Val Thr Arg Phe Lys Asp
                340                 345                 350

Thr Tyr Phe Val Thr Gly Ile Val Ser Trp Gly Glu Gly Cys Ala Arg
                355                 360                 365

Lys Gly Lys Tyr Gly Ile Tyr Thr Lys Val Thr Ala Phe Leu Lys Trp
370                 375                 380

Ile Asp Arg Ser Met Lys Thr Arg Gly Leu Pro Lys Ala Lys Ser His
385                 390                 395                 400

Ala Pro Glu Val Ile Thr Ser Ser Pro Leu Lys
                405                 410
```